(12) United States Patent
Suh et al.

(10) Patent No.: US 7,745,020 B2
(45) Date of Patent: Jun. 29, 2010

(54) METALLIC COMPOUND AND ORGANIC ELECTROLUMINESCENCE DEVICE COMPRISING THE SAME

(75) Inventors: Dong-Hack Suh, Seongnam (KR); Song-Ho Kim, Seoul (KR); Chi-Hun Kim, Seoul (KR); Dae-Beom Kim, Seoul (KR)

(73) Assignees: Samsung Electronics Co., Ltd. (KR); Industry-University Cooperation Foundation, Hanyang University (KR)

( * ) Notice: Subject to any disclaimer, the term of this patent is extended or adjusted under 35 U.S.C. 154(b) by 347 days.

(21) Appl. No.: 11/910,161

(22) PCT Filed: Apr. 10, 2007

(86) PCT No.: PCT/KR2007/000114

§ 371 (c)(1),
(2), (4) Date: Sep. 28, 2007

(87) PCT Pub. No.: WO2007/078185

PCT Pub. Date: Jul. 12, 2007

(65) Prior Publication Data

US 2008/0193795 A1    Aug. 14, 2008

(30) Foreign Application Priority Data

Jan. 6, 2006    (KR) .................. 10-2006-0001840

(51) Int. Cl.
*H01L 51/54*    (2006.01)
*C09K 11/06*    (2006.01)
*B32B 9/00*    (2006.01)
*C07F 17/02*    (2006.01)

(52) U.S. Cl. .................. 428/690; 546/10; 428/917; 313/504; 313/506

(58) Field of Classification Search .................. None
See application file for complete search history.

(56) References Cited

U.S. PATENT DOCUMENTS

2005/0287391 A1    12/2005    Chang et al.

FOREIGN PATENT DOCUMENTS

| JP | 2003007471 | 1/2003 |
| JP | 2003264086 | 9/2003 |
| JP | 2004158391 | 6/2004 |

OTHER PUBLICATIONS

Written Opinion dated Apr. 10, 2007 for Application No. PCT/KR2007/000114.
International Search Report dated Apr. 10, 2007 for Application No. PCT/KR2007/000114 (All references cited in Search Report are listed above).

*Primary Examiner*—Dawn Garrett
(74) *Attorney, Agent, or Firm*—Cantor Colburn LLP

(57) ABSTRACT

The present invention relates to a light emitting metallic compound of Chemical Formula 1 and an organic electroluminescence device including the compound. In the Chemical Formula 1, M is selected from Ir, Pt, Rh, Re, and Os, m is 2, provided that m is 1 when M is Pt. X is a N or P atom, Y is S, O, or Se, and Z is $SiR^5R^6$, $CR^5R^6$, $PR^5$, S, $SO_2$, carbonyl, or $NR^5$, and $L^2$ is represented by Chemical Formulae 2, 3, or 4. $R^1$, $R^2$, $R^3$, $R^4$, $R^5$, $R^6$, $R^7$, and $R^8$ are the same or different, and are selected from hydrogen, a C1 to C20 alkyl, an aryl, a cycloalkyl, a halogen, a linear or branched substituent including at least one halogen, a linear or branched substituent including at least one heteroatom, carbonyl, vinyl, and acetylenyl, or may form a cycle, and $R^9$ is hydrogen, a C1 to C20 alkyl excluding an aromatic cyclic substituent, a cycloalkyl, a halogen, a linear or branched substituent including at least one halogen; or a linear or branched substituent including at least one heteroatom.

2 Claims, No Drawings

METALLIC COMPOUND AND ORGANIC ELECTROLUMINESCENCE DEVICE COMPRISING THE SAME

TECHNICAL FIELD

The present invention relates to a metallic compound and an organic electroluminescence device including the same, and more particularly, to a metallic compound that is applicable as a highly efficient phosphor host material and an organic electroluminescence device including the same.

BACKGROUND OF ART

An electroluminescence device (EL device) is a self-light emitting display device having such merits as a wide viewing angle and excellent contrast as well as a quick response time.

EL devices are classified into an inorganic EL device and an organic EL device in accordance with a material used for a light emitting layer. The organic EL device has merits of improved luminance, driving voltage, response speed, and multi-colorfying property compared to an inorganic EL device.

An organic EL device is generally composed of an anode on a substrate, a hole transport layer on the anode, and a light emitting layer, an electron transport layer (ETL), and a cathode sequentially positioned thereon. The hole transport layer, light emitting layer, and electron transport layer (ETL) are organic films that are composed of organic compounds.

The organic EL device having the above structure is operated as follows.

When a voltage is applied to a space between the anode and the cathode, the holes are injected from the anode to the light emitting layer through the hole transport layer. Meanwhile, when the electrons are injected from the cathode into the light emitting layer through the electron transport layer (ETL), carriers are recombined in the region of the light emitting layer to thereby produce excitons. The state of the excitons is changed from an exited state to a base state, and the change in the state of the excitons makes the molecules of the light emitting layer emit light to thereby form an image.

Materials for forming a light emitting layer are divided into fluorescent materials using singlet excitons and phosphorescent materials using triplet excitons according to the light emitting mechanism. Phosphorescent materials generally include organic/inorganic compound structures including transition element atoms. The transition element atoms change triplet excitons, which used to be impossible to transition, into excitons that are possible to transition, causing them to emit phosphorescent light. Since the phosphorescent materials can use triplet excitons having a generation probability of 75%, higher luminous efficiency can be achieved than with fluorescent materials using singlet excitons having a generation probability of 25%.

Among light emitting materials using the triplet excitons are phosphorescent materials including iridium and platinum compounds (Sergey Lamansky et al. Inorg. Chem., 40, 1704-1711, 2001, and Sergey Lamansky et al., J. Am. Chem. Soc., 123, 4304-4312, 2001). For blue light emitting materials, Ir compounds based on (4,6-F2ppy)$_2$Irpic or a fluorinated ppy ligand structure have been developed (Vladimir V. Grushin et al., Chem. Commun., 1494-1495, 2001). The (4,6-F2ppy)$_2$Irpic, however, has shortcomings that it emits light in a sky blue region and its large shoulder peaks increase a y value in color purity coordinates. Researchers are studying red and green light emitting materials, but there still remains great demand to develop highly efficient phosphorescent materials having a long lifespan.

DETAILED DESCRIPTION OF THE INVENTION

[Technical Problem]

In order to solve the problems, the object of the present invention is to provide a phosphor dimeric metallic compound having a new co-ligand structure and an organic electroluminescence device having improved luminous efficiency and color purity.

[Technical Solution]

The present invention relates to a light-emitting binuclear transition metal compound represented by the following Chemical Formula 1, and an organic electroluminescence device including the same:

[Chemical Formula 1]

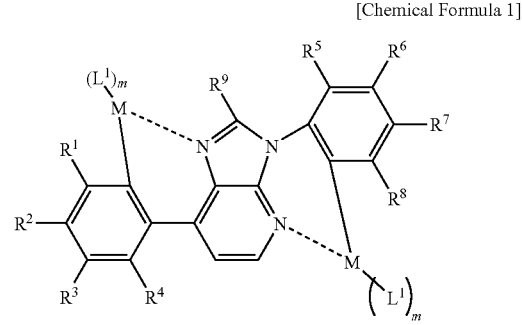

Wherein, in the above Chemical Formula 1, M is Ir, Pt, Rh, Re, Os, and the like, m is 2, provided that the m is 1 when M is Pt, $R^1$, $R^2$, $R^3$, $R^4$, $R^5$, $R^6$, $R^7$, and $R^8$ are the same or different, and are selected from hydrogen, a C1 to C20 alkyl, an aryl, a cycloalkyl, a halogen, a linear or branched substituent including at least one halogen, a linear or branched substituent including at least one heteroatom, carbonyl, vinyl, and acetylenyl, or form a cycle, and $R^9$ is hydrogen, a C1 to C20 alkyl excluding an aromatic cyclic substituent, a cycloalkyl, a halogen, a linear or branched substituent including at least one halogen, or a linear or branched substituent including at least one heteroatom.

In the above Chemical Formula 1, $L^1$ is represented by the following Chemical Formula 2:

[Chemical Formula 2]

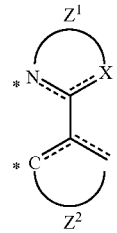

$L^1$ in the above formula 2, is a independent ligand having a covalent bond site with a carbon denoted as * and a coordination bond with nitrogen and forming a complex compound with the transition metal M, and X is a hetero atom of nitrogen, oxygen, sulfur, phosporus, and so on, and $Z^1$ and $Z^2$ are atoms for forming a C4 to C7 aromatic hydrocarbon ring or aromatic heterocyclic ring.

In the present invention, a benzo oxazole and benzo thiazole aromatic-based derivative are introduced for a co-ligand that is capable of forming a transition metal compound by a covalent bond with C and by a coordination bond with N.

The examples of the co-ligand are represented by the following Chemical Formulae 3:

[Chemical Formulae 3]

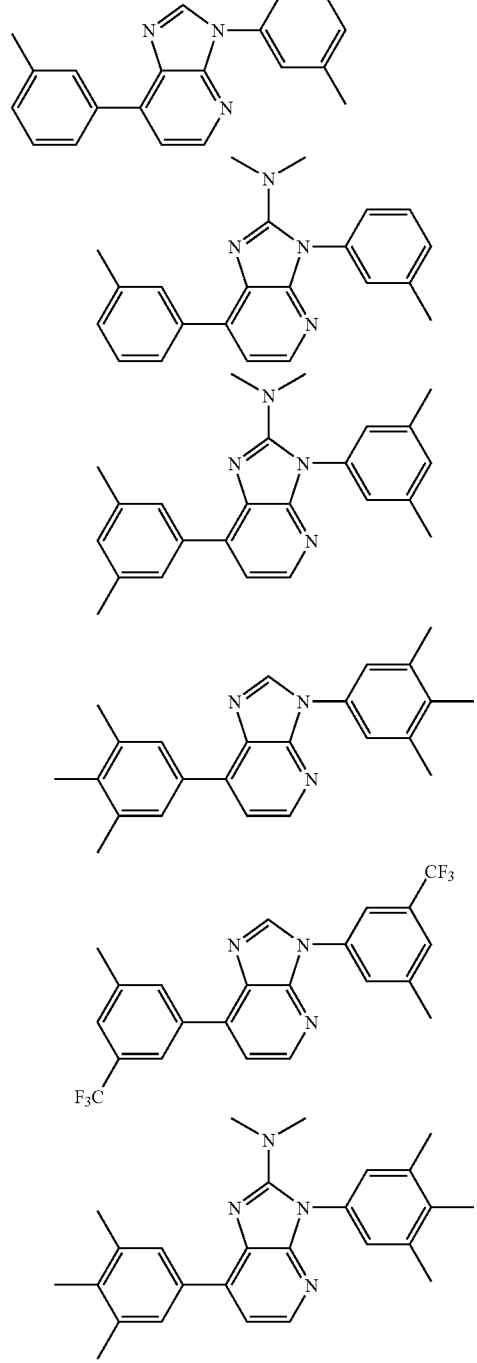

-continued

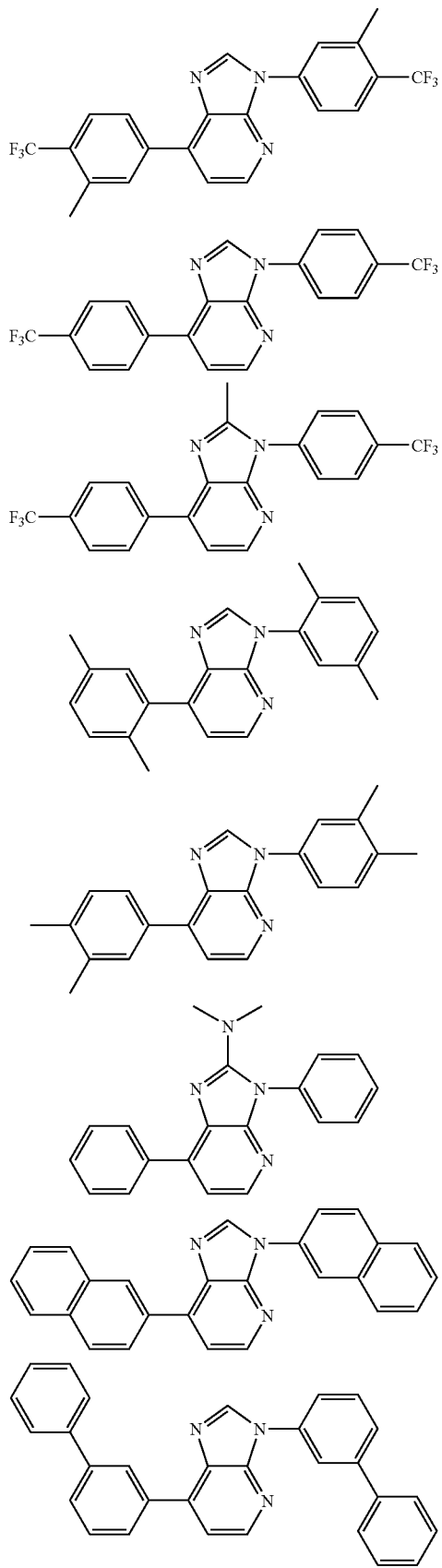

-continued
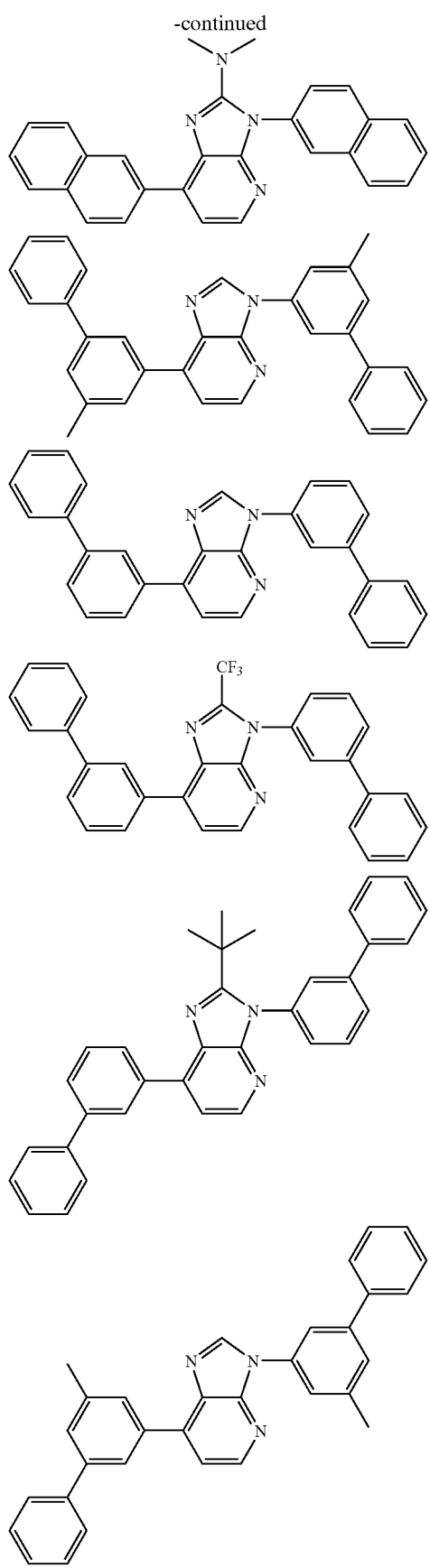
-continued
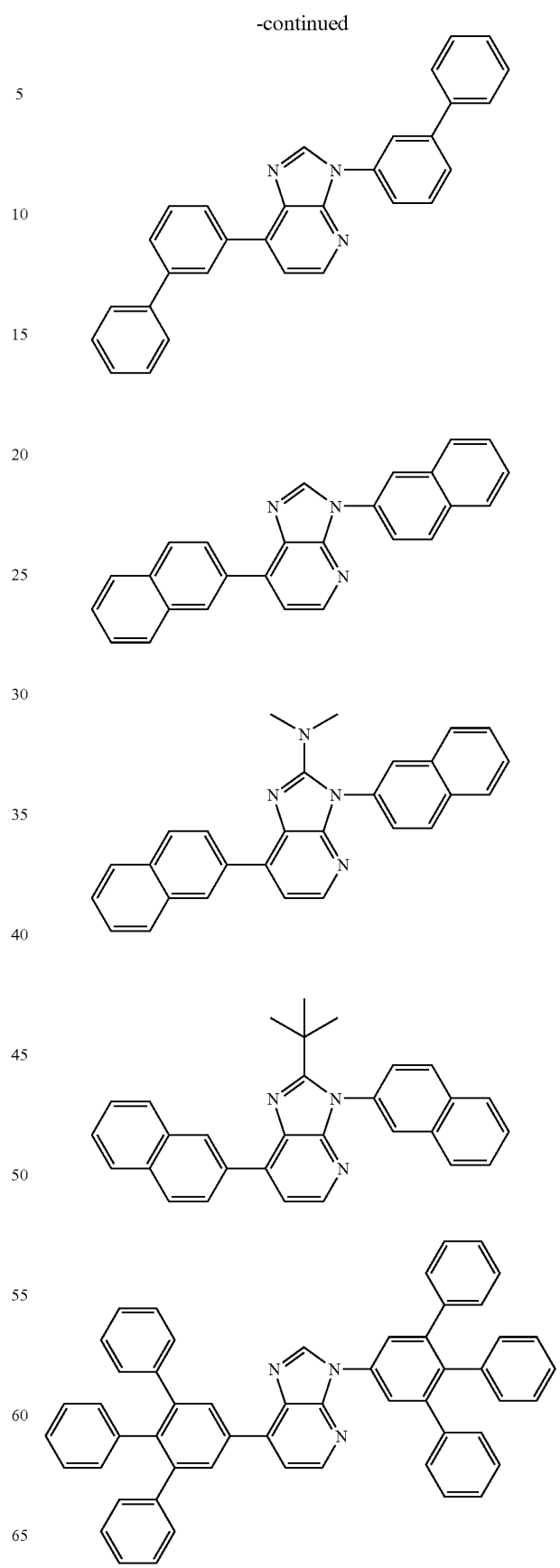

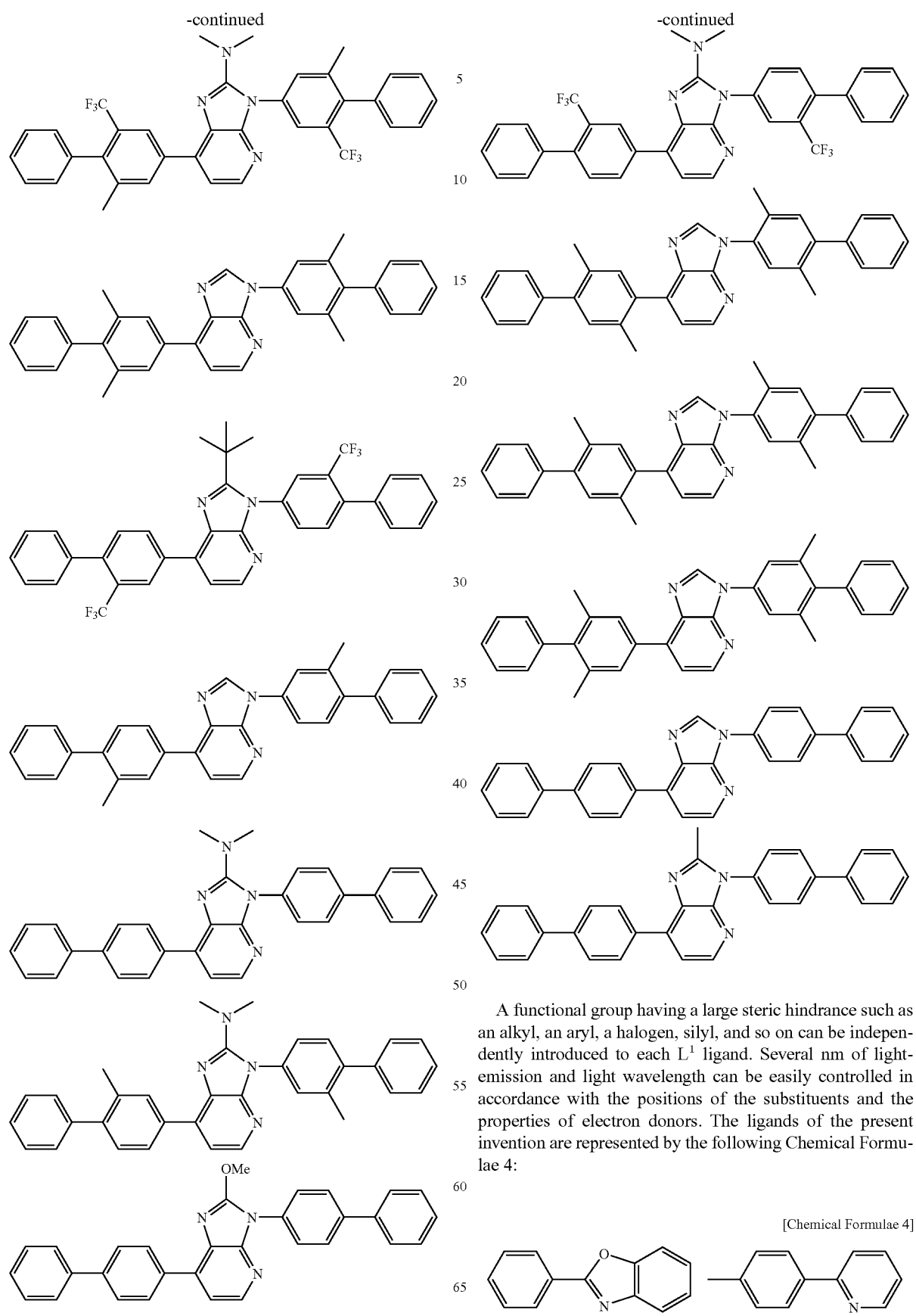

A functional group having a large steric hindrance such as an alkyl, an aryl, a halogen, silyl, and so on can be independently introduced to each $L^1$ ligand. Several nm of light-emission and light wavelength can be easily controlled in accordance with the positions of the substituents and the properties of electron donors. The ligands of the present invention are represented by the following Chemical Formulae 4:

[Chemical Formulae 4]

-continued
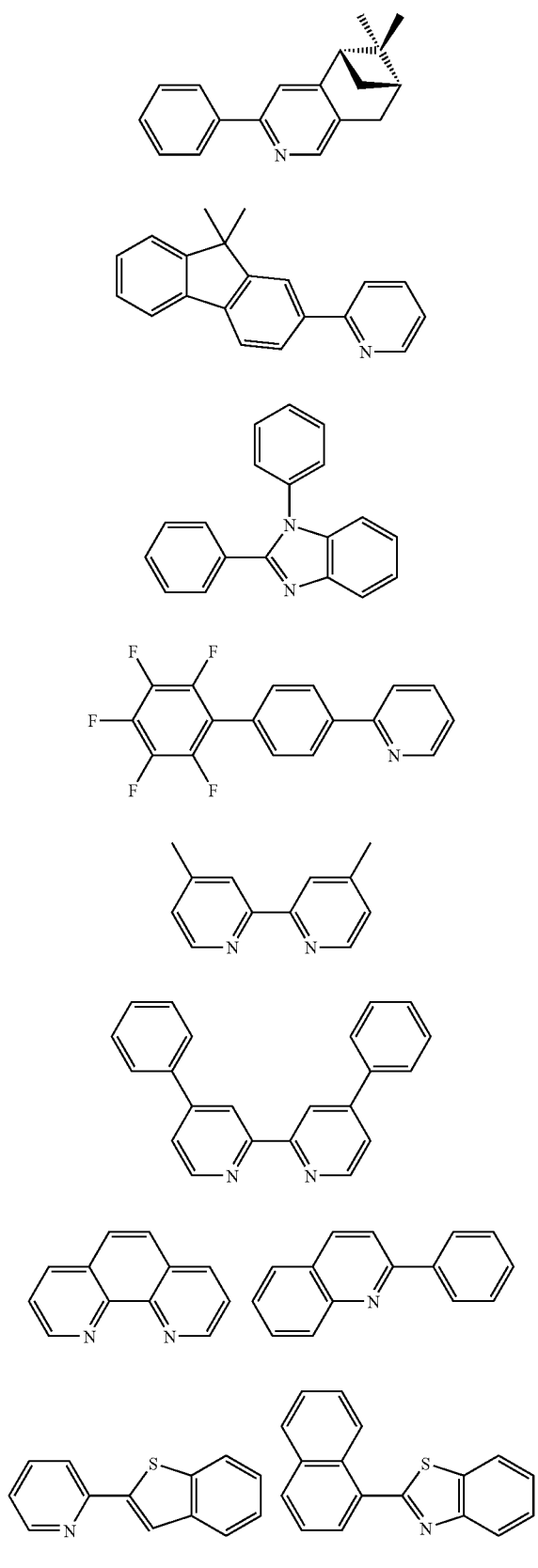
-continued
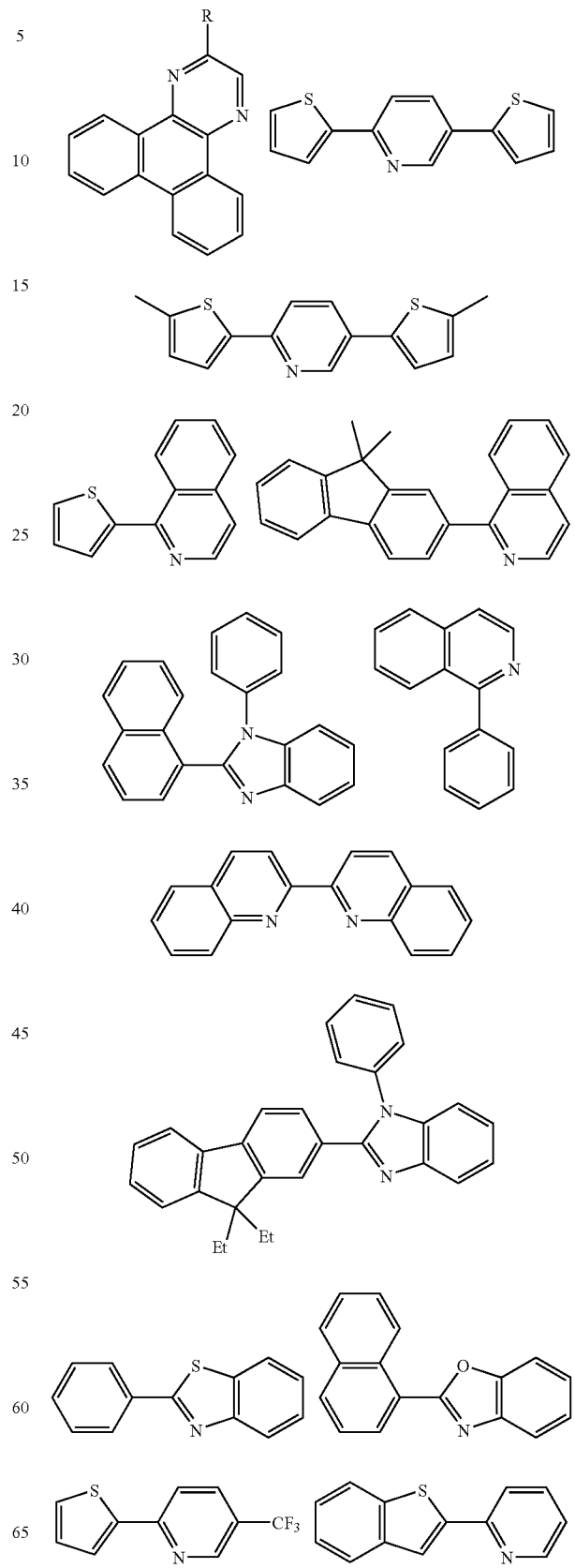

-continued
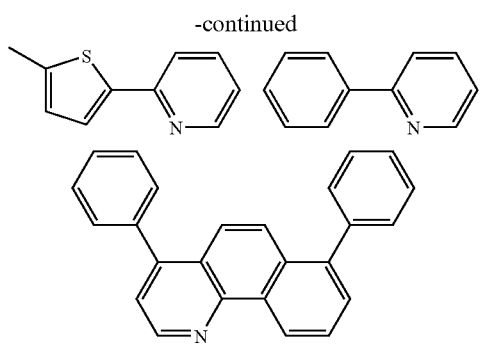
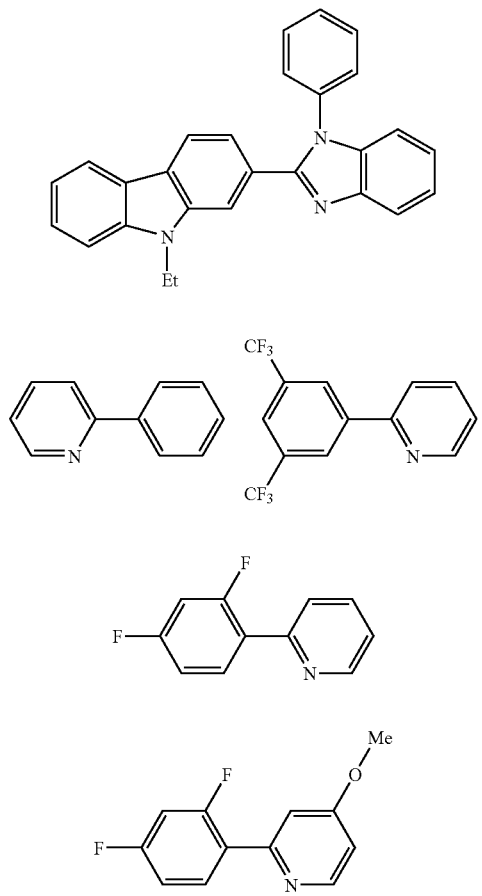
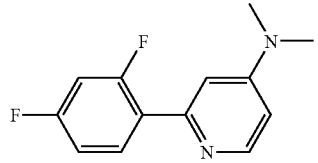
The transition metal compound represented by the above Chemical Formulae can be synthesized as follows. The following Reaction Scheme 1 shows a ligand synthesis, and the Reaction Scheme 2 shows a metalation process.
[Reaction Scheme 1]
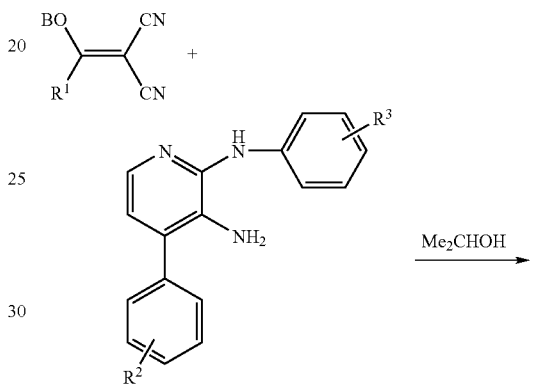
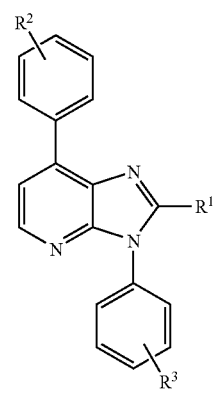
[Reaction Scheme 2]
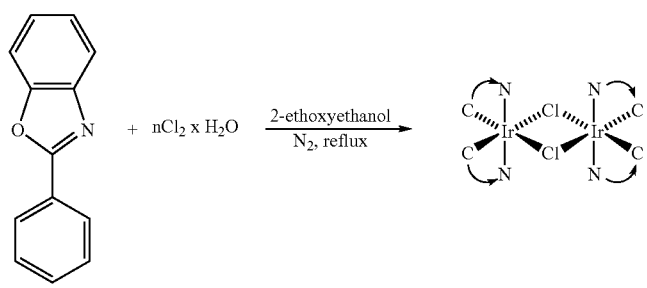

-continued

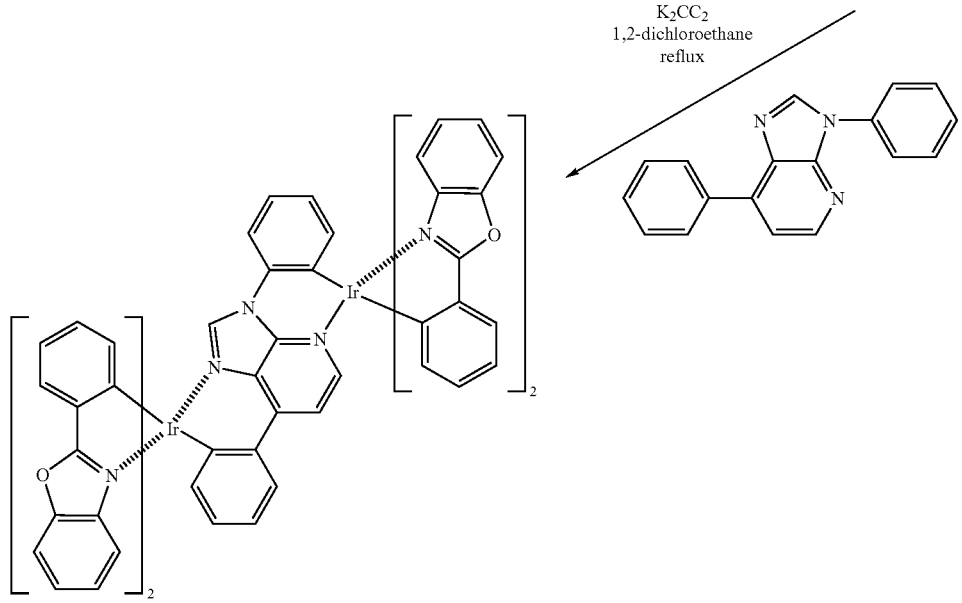

As shown in Reaction Scheme 2, a main ligand having C—N chelating site and hydrated iridium trichloride are reacted under a nitrogen atmosphere to prepare a dimmer intermediate that includes two iridium metals sharing a Cl ligand, and then the intermediate is reacted with a co-ligand in a solvent including a weak base to prepare the transition metal compound of Chemical Formula 1.

[Best Mode]

The present invention can be specified by the following Examples. The Examples only illustrate the present invention and they do not limit the scope and range of the present invention, which is defined by the accompanying claims.

EXAMPLE 1

Synthesis of compound $(PBOZ)_2Ir(DPhlPy)Ir(PBOZ)_2$

Synthesis of 3.7-diphenyl-3H-imidazo[4,5-b]pyridine (DPhlPy): 0.70 mol of $N^2$,4-diphenylpyridine-2,3-diamine and 2.56 mol of ethoxymethylene malononitrile were added in 10 ml of isopropanol, and refluxed for 6 hours. The solution was removed and was purified by using column chromatography to thereby produce a solid crystalline product at a yield of 75%.

Synthesis of $(PBOZ)_2Ir(Cl)_2Ir(PBOZ)_2$: 5 mmol of 2-phenylbenzo[d]oxazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBOZ)_2Ir(Cl)_2Ir(PBOZ)_2$ at a yield of 92%.

Synthesis of $(PBOZ)_2Ir(DPhlPy)Ir(PBOZ)_2$: 5 mmol of $(PBOZ)_2Ir(Cl)_2IrPBOZ)_2$ and 25 mmol of 3.7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBOZ)_2Ir(DPhlPy)Ir(PBOZ)_2$ at a yield of 89%.

EXAMPLE 2

Synthesis of compound $(F_2ppy)_2Ir(DPhlPy)Ir(F_2ppy)_2$

Synthesis of $(F_2ppy)_2Ir(Cl)_2Ir(F_2ppy)_2$: 5 mmol of 2-(2,4-difluorophenyl)pyridine and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(F_2ppy)_2Ir(Cl)_2Ir(F_2ppy)_2$ at a yield of 90%.

Synthesis of $(F_2ppy)_2Ir(DPhlPy)Ir(F_2ppy)_2$: 5 mmol of $(F_2ppy)_2Ir(Cl)_2Ir(F_2ppy)_2$ and 25 mmol of 3.7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(F_2ppy)_2Ir(DPhlPy)Ir(F_2ppy)_2$ at a yield of 87%.

EXAMPLE 3

Synthesis of compound $(SPBOZ)_2Ir(DPhlPy)Ir(SPBOZ)_2$

Synthesis of $(SPBOZ)_2Ir(Cl)_2Ir(SPBOZ)_2$: 5 mmol of 4-(4-(trimethylsilyl)phenyl)benzo[d]oxazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(F_2ppy)_2Ir(Cl)_2Ir(F_2ppy)_2$ at a yield of 88%.

Synthesis of (SPBOZ)$_2$Ir(DPhlPy)Ir(SPBOZ)$_2$: 5 mmol of (SPBOZ)$_2$Ir(Cl)$_2$Ir(SPBOZ)$_2$ and 25 mmol of 3.7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(DPhlPy)Ir(SPBOZ)$_2$ at a yield of 86%.

EXAMPLE 4

Synthesis of compound (SPBOZ)$_2$Ir(DPhlPy)Ir(SPBOZ)$_2$

Synthesis of (SPBOZ)$_2$Ir(Cl)$_2$Ir(SPBOZ)$_2$: 5 mmol of 4-(4-(trimethylsilyl)phenyl)benzo[d]oxazole(SPBOZ) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (F$_2$ppy)$_2$Ir(Cl)$_2$Ir(F$_2$ppy)$_2$ at a yield of 87%.

Synthesis of (SPBOZ)$_2$Ir(DPhlPy)Ir(SPBOZ)$_2$: 5 mmol of (SPBOZ)$_2$Ir(Cl)$_2$Ir(SPBOZ)$_2$ and 25 mmol of 3.7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(DPhlPy)Ir(SPBOZ)$_2$ at a yield of 84%.

EXAMPLE 5

Synthesis of compound (PzDCA)$_2$Ir(DPhlPy)Ir(PzDCA)$_2$

Synthesis of (PzDCA)$_2$Ir(Cl)$_2$Ir(PzDCA)$_2$: 5 mmol of pyrazine-2,5-dicarboxylic acid(PzDCA) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PzDCA)$_2$Ir(Cl)$_2$Ir(PzDCA)$_2$ at a yield of 90%.

Synthesis of (PzDCA)$_2$Ir(DPhlPy)Ir(PzDCA)$_2$: 5 mmol of (PzDCA)$_2$Ir(Cl)$_2$Ir(PzDCA)$_2$ and 25 mmol of 3.7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PzDCA)$_2$Ir(DPhlPy)Ir(PzDCA)$_2$ at a yield of 88%.

EXAMPLE 6

Synthesis of compound (PBOZ)$_2$Ir(MDPhlPy)Ir(PBOZ)$_2$

Synthesis of 2-methyl-3,7-diphenyl-3H-imidazo[4,5-b]pyridine (MDPhlPy): 0.70 mol of N$^2$,4-diphenylpyridine-2,3-diamine and 2.56 mol of ethoxy ethylene malononitrile was added in 10 ml of isopropanol, and refluxed for 6 hours. The solution was removed and was purified by using column chromatography to thereby produce a solid crystalline product at a yield of 74%.

Synthesis of (PBOZ)$_2$Ir(Cl)$_2$Ir(PBOZ)$_2$: 5 mmol of 2-phenylbenzo[d]oxazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBOZ)$_2$Ir(Cl)$_2$Ir(PBOZ)$_2$ at a yield of 87%.

Synthesis of (PBOZ)$_2$Ir(MDPhlPy)Ir(PBOZ)$_2$: 5 mmol of (PBOZ)$_2$Ir(Cl)$_2$IrPBOZ)$_2$ and 25 mmol of 2-methyl-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBOZ)$_2$ Ir(MDPhlPy)Ir(PBOZ)$_2$ at a yield of 83%.

EXAMPLE 7

Synthesis of compound (PBTZ)$_2$Ir(MDPhlPy)Ir(PBTZ)$_2$

Synthesis of (PBTZ)$_2$Ir(Cl)$_2$Ir(PBTZ)$_2$: 5 mmol of 2-phenylbenzo[d]thiazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBTZ)$_2$Ir(Cl)$_2$Ir(PBTZ)$_2$ at a yield of 84%.

Synthesis of (PBTZ)$_2$Ir(MDPhlPy)Ir(PBTZ)$_2$: 5 mmol of (PBTZ)$_2$Ir(Cl)$_2$Ir(PBTZ)$_2$ and 25 mmol of 2-methyl-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBTZ)$_2$Ir(MDPhlPy)Ir(PBTZ)$_2$ at a yield of 80%.

EXAMPLE 8

Synthesis of compound (F$_2$ppy)$_2$Ir(MDPhlPy)Ir(F$_2$ppy)$_2$

Synthesis of (F$_2$ppy)$_2$Ir(Cl)$_2$Ir(F$_2$ppy)$_2$: 5 mmol of 2-(2,4-difluorophenyl)pyridine and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (F$_2$ppy)$_2$Ir(Cl)$_2$Ir(F$_2$ppy)$_2$ at a yield of 82%.

Synthesis of (F$_2$ppy)$_2$Ir(MDPhlPy)Ir(F$_2$ppy)$_2$: 5 mmol of (F$_2$ppy)$_2$Ir(Cl)$_2$Ir(F$_2$ppy)$_2$ and 25 mmol of 2-methyl-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (F$_2$ppy)$_2$Ir(MDPhlPy)Ir(F$_2$ppy)$_2$ at a yield of 79%.

EXAMPLE 9

Synthesis of compound (SPBOZ)$_2$Ir(MDPhlPy)Ir(SPBOZ)$_2$

Synthesis of (SPBOZ)$_2$Ir(Cl)$_2$Ir(SPBOZ)$_2$: 5 mmol of 4-(4-(trimethylsilyl)phenyl)benzo[d]oxazole(SPBOZ) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (SPBOZ)$_2$Ir(Cl)$_2$Ir(SPBOZ)$_2$ at a yield of 80%.

Synthesis of (SPBOZ)$_2$Ir(MDPhlPy)Ir(SPBOZ)$_2$: 5 mmol of (SPBOZ)$_2$Ir(Cl)$_2$Ir(SPBOZ)$_2$ and 25 mmol of 2-methyl-3, 7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(MDPhlPy)Ir(SPBOZ)$_2$ at a yield of 78%.

EXAMPLE 10

Synthesis of compound (PzDCA)$_2$Ir(MDPhlPy)Ir(PzDCA)$_2$

Synthesis of (PzDCA)$_2$Ir(Cl)$_2$Ir(PzDCA)$_2$: 5 mmol of pyrazine-2,5-dicarboxylic acid(PzDCA) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PzDCA)$_2$Ir(Cl)$_2$Ir(PzDCA)$_2$ at a yield of 82%.

Synthesis of (PzDCA)$_2$Ir(DPhlPy)Ir(PzDCA)$_2$: 5 mmol of (PzDCA)$_2$Ir(Cl)$_2$Ir(PzDCA)$_2$ and 25 mmol of 2-methyl-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PzDCA)$_2$Ir(MDPhlPy)Ir(PzDCA)$_2$ at a yield of 81%.

EXAMPLE 11

Synthesis of compound (PBOZ)$_2$Ir(FDPhlPy)Ir(PBOZ)$_2$

Synthesis of 2-(trifluoromethyl)-3,7-diphenyl-3H-imidazo[4,5-b]pyridine (FDPhlPy): 0.70 mol of $N^2$ 4-diphenylpyridine-2,3-diamine and 2.56 mol of 2-(1-ethoxy-2,2,2-trifluoroethyllidyne)malonnitrile were added in 10 ml of isopropanol, and refluxed for 6 hours. The solution was removed and was purified by using column chromatography to thereby produce a solid crystalline product at a yield of 72%.

Synthesis of (PBOZ)$_2$Ir(Cl)$_2$Ir(PBOZ)$_2$: 5 mmol of 2-phenylbenzo[d]oxazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBOZ)$_2$Ir(Cl)$_2$Ir(PBOZ)$_2$ at a yield of 82%.

Synthesis of (PBOZ)$_2$Ir(FDPhlPy)Ir(PBOZ)$_2$: 5 mmol of (PBOZ)$_2$Ir(Cl)$_2$IrPBOZ)$_2$ and 25 mmol of 2-(trifluoromethyl)-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBOZ)$_2$Ir(FDPhlPy)Ir(PBOZ)$_2$ at a yield of 80%.

EXAMPLE 12

Synthesis of compound (PBTZ)$_2$Ir(FDPhlPy)Ir(PBTZ)$_2$

Synthesis of (PBTZ)$_2$Ir(Cl)$_2$Ir(PBTZ)$_2$: 5 mmol of 2-phenylbenzo[d]thiazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBTZ)$_2$Ir(Cl)$_2$Ir(PBTZ)$_2$ at a yield of 79%.

Synthesis of (PBTZ)$_2$Ir(FDPhlPy)Ir(PBTZ)$_2$: 5 mmol of (PBTZ)$_2$Ir(Cl)$_2$Ir(PBTZ)$_2$ and 25 mmol of 2-(trifluoromethyl)-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBTZ)$_2$Ir(FDPhlPy)Ir(PBTZ)$_2$ at a yield of 76%.

EXAMPLE 13

Synthesis of compound (F$_2$ppy)$_2$Ir(FDPhlPy)Ir(F$_2$ppy)$_2$

Synthesis of (F$_2$ppy)$_2$Ir(Cl)$_2$Ir(F$_2$ppy)$_2$: 5 mmol of 2-(2, 4-fluorophenyl)pyridine and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (F$_2$ppy)$_2$Ir(Cl)$_2$Ir(F$_2$ppy)$_2$ at a yield of 77%.

Synthesis of (F$_2$ppy)$_2$Ir(FDPhlPy)Ir(F$_2$ppy)$_2$: 5 mmol of (F$_2$ppy)$_2$Ir(Cl)$_2$Ir(F$_2$ppy)$_2$ and 25 mmol of 2-(trifluoromethyl)-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (F$_2$ppy)$_2$Ir(FDPhlPy)Ir(F$_2$ppy)$_2$ at a yield of 74%.

EXAMPLE 14

Synthesis of compound (SPBOZ)$_2$Ir(FDPhlPy)Ir(SPBOZ)$_2$

Synthesis of (SPBOZ)$_2$Ir(Cl)$_2$Ir(SPBOZ)$_2$: 5 mmol of 4-(4-(trimethylsilyl)phenyl)benzo[d]oxazole(SPBOZ) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(SPBOZ)_2Ir(Cl)_2Ir(SPBOZ)_2$ at a yield of 73%.

Synthesis of $(SPBOZ)_2Ir(FDPhlPy)Ir(SPBOZ)_2$: 5 mmol of $(SPBOZ)_2Ir(Cl)_2Ir(SPBOZ)_2$ and 25 mmol of 2-(trifluoromethyl)-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(SPBOZ)_2Ir(FDPhlPy)Ir(SPBOZ)_2$ at a yield of 70%.

EXAMPLE 15

Synthesis of compound $(PzDCA)_2Ir(FDPhlPy)Ir(PzDCA)_2$

Synthesis of $(PZDCA)_2Ir(Cl)_2Ir(PzDCA)_2$: 5 mmol of pyrazine-2,5-dicarboxylic acid(PzDCA) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PzDCA)_2Ir(Cl)_2Ir(PzDCA)_2$ at a yield of 76%.

Synthesis of $(PzDCA)_2Ir(FDPhlPy)Ir(PzDCA)_2$: 5 mmol of $(PzDCA)_2Ir(Cl)_2Ir(PzDCA)_2$ and 25 mmol of 2-(trifluoromethyl)-3,7-diphenyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PzDCA)_2Ir(FDPhlPy)Ir(PzDCA)_2$ at a yield of 75%.

EXAMPLE 16

Synthesis of compound $(PBOZ)_2Ir(DMDPIZPyA)Ir(PBOZ)_2$

N,N-dimethyl-3,7-diphenyl-3H-imidazo[4,5-b]pyridine-2-amine (DMDPIZPyA) synthesis: 0.70 mol of $N^2$,4-diphenylpyridine-2,3-diamine and 2.56 mol of 2-((dimethylamino)(ethoxy)methylene)malonnitrile were added in 10 ml of isopropanol, and refluxed for 6 hours. The solution was removed and was purified by using column chromatography to thereby produce a solid crystalline product at a yield of 70%.

Synthesis of $(PBOZ)_2Ir(Cl)_2Ir(PBOZ)_2$: 5 mmol of 2-phenylbenzo[d]oxazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBOZ)_2Ir(Cl)_2Ir(PBOZ)_2$ at a yield of 82%.

Synthesis of $(PBOZ)_2Ir(DMDPIZPyA)Ir(PBOZ)_2$: 5 mmol of $(PBOZ)_2Ir(Cl)_2IrPBOZ)_2$ and 25 mmol of N,N-dimethyl-3,7-diphenyl-3H-imidazo[4,5-b]pyridine-2-amine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBOZ)_2Ir(FDPhlPy)Ir(PBOZ)_2$ at a yield of 81%.

EXAMPLE 17

Synthesis of compound $(PBTZ)_2Ir(DMDPIZPyA)Ir(PBTZ)_2$

Synthesis of $(PBTZ)_2Ir(Cl)_2Ir(PBTZ)_2$: 5 mmol of 2-phenylbenzo[d]thiazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBTZ)_2Ir(Cl)_2Ir(PBTZ)_2$ at a yield of 81%.

Synthesis of $(PBTZ)_2Ir(DMDPIZPyA)Ir(PBTZ)_2$: 5 mmol of $(PBTZ)_2Ir(Cl)_2Ir(PBTZ)_2$ and 25 mmol of N,N-dimethyl-3,7-diphenyl-3H-imidazo[4,5-b]pyridine-2-amine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBTZ)_2Ir(FDPhlPy)Ir(PBTZ)_2$ at a yield of 81%.

EXAMPLE 18

Synthesis of compound $(F_2ppy)_2Ir(DMDPIZPyA)Ir(F_2ppy)_2$

Synthesis of $(F_2ppy)_2Ir(Cl)_2Ir(F_2ppy)_2$: 5 mmol of 2-(2,4-fluorophenyl)pyridine and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(F_2ppy)_2Ir(Cl)_2Ir(F_2ppy)_2$ at a yield of 81%.

Synthesis of $(F_2ppy)_2Ir(DMDPIZPyA)Ir(F_2ppy)_2$: 5 mmol of $(F_2ppy)_2Ir(Cl)_2Ir(F_2ppy)_2$ and 25 mmol of N,N-dimethyl-3,7-diphenyl-3H-imidazo[4,5-b]pyridine-2-amine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(F_2ppy)_2Ir(DMDPIZPyA)Ir(F_2ppy)_2$ at a yield of 78%.

EXAMPLE 19

Synthesis of compound $(SPBOZ)_2Ir(DMDPIZPyA)Ir(SPBOZ)_2$

Synthesis of $(SPBOZ)_2Ir(Cl)_2Ir(SPBOZ)_2$: 5 mmol of 4-(4-(trimethylsilyl)phenyl)benzo[d]oxazole(SPBOZ) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(SPBOZ)_2Ir(Cl)_2Ir(SPBOZ)_2$ at a yield of 77%.

Synthesis of $(SPBOZ)_2Ir(DMDPIZPyA)Ir(SPBOZ)_2$: 5 mmol of $(SPBOZ)_2Ir(Cl)_2Ir(SPBOZ)_2$ and 25 mmol of N,N-dimethyl-3,7-diphenyl-3H-imidazo[4,5-b]pyridine-2-amine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(SPBOZ)_2Ir(DMDPIZPyA)Ir(SPBOZ)_2$ at a yield of 75%.

EXAMPLE 20

Synthesis of compound $(PzDCA)_2Ir(DMDPIZPyA)Ir(PzDCA)_2$

Synthesis of $(PzDCA)_2Ir(Cl)_2Ir(PzDCA)_2$: 5 mmol of pyrazine-2,5-dicarboxylic acid (PZDCA) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PzDCA)_2Ir(Cl)_2Ir(PzDCA)_2$ at a yield of 82%.

Synthesis of $(PzDCA)_2Ir(FDPhlPy)Ir(PzDCA)_2$: 5 mmol of $(PzDCA)_2Ir(Cl)_2Ir(PzDCA)_2$ and 25 mmol of N,N-dimethyl-3,7-diphenyl-3H-imidazo[4,5-b]pyridine-2-amine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PzDCA)_2Ir(DMDPIZPyA)Ir(PzDCA)_2$ at a yield of 79%.

EXAMPLE 21

Synthesis of compound $(PBOZ)_2Ir(DTylzPy)Ir(PBOZ)_2$

Synthesis of 3,7-dip-tolyl-3H-imidazo[4,5-b]pyridine (DTylzPy): 0.70 mol of $N^2$,4-dip-tolylpyridine-2,3-diamine and 2.56 mol of 2-(ethoxymethylene)malonnitrile were added in 10 ml of isopropanol, and refluxed for 6 hours. The solution was removed and was purified by using column chromatography to thereby produce a solid crystalline product at a yield of 84%.

Synthesis of $(PBOZ)_2Ir(Cl)_2Ir(PBOZ)_2$: 5 mmol of 2-phenylbenzo[d]oxazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBOZ)_2Ir(Cl)_2Ir(PBOZ)_2$ at a yield of 94%.

Synthesis of $(PBOZ)_2Ir(DTylzPy)Ir(PBOZ)_2$: 5 mmol of $(PBOZ)_2Ir(Cl)_2IrPBOZ)_2$ and 25 mmol of 3,7-dip-tolyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBOZ)_2Ir(DTylzPy)Ir(PBOZ)_2$ at a yield of 91%.

EXAMPLE 22

Synthesis of compound $(PBTZ)_2Ir(DTylzPy)Ir(PBTZ)_2$

Synthesis of $(PBTZ)_2Ir(Cl)_2Ir(PBTZ)_2$: 5 mmol of 2-phenylbenzo[d]thiazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBTZ)_2Ir(Cl)_2Ir(PBTZ)_2$ at a yield of 92%.

Synthesis of $(PBTZ)_2Ir(DTylzPy)Ir(PBTZ)_2$: 5 mmol of $(PBTZ)_2Ir(Cl)_2Ir(PBTZ)_2$ and 25 mmol of 3,7-dip-tolyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBTZ)_2Ir(DTylzPy)Ir(PBTZ)_2$ at a yield of 90%.

EXAMPLE 23

Synthesis of compound $(F_2ppy)_2Ir(DTylzPy)Ir(F_2ppy)_2$

Synthesis of $(F_2ppy)_2Ir(Cl)_2Ir(F_2ppy)_2$: 5 mmol of 2-(2,4-difluorophenyl)pyridine and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(F_2ppy)_2Ir(Cl)_2Ir(F_2ppy)_2$ at a yield of 90%.

Synthesis of $(F_2ppy)_2Ir(DTylzPy)Ir(F_2ppy)_2$: 5 mmol of $(F_2ppy)_2Ir(Cl)_2Ir(F_2ppy)_2$ and 25 mmol of 3,7-dip-tolyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(F_2ppy)_2Ir(DTylzPy)Ir(F_2ppy)_2$ at a yield of 88%.

EXAMPLE 24

Synthesis of compound $(SPBOZ)_2Ir(DTylzPy)Ir(SPBOZ)_2$

Synthesis of $(SPBOZ)_2Ir(Cl)_2Ir(SPBOZ)_2$: 5 mmol of 4-(4-(trimethylsilyl)phenyl)benzo[d]oxazole(SPBOZ) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(SPBOZ)_2Ir(Cl)_2Ir(SPBOZ)_2$ at a yield of 89%.

Synthesis of $(SPBOZ)_2Ir(DTylzPy)Ir(SPBOZ)_2$: 5 mmol of $(SPBOZ)_2Ir(Cl)_2Ir(SPBOZ)_2$ and 25 mmol of 3,7-dip-tolyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(DTylzPy)Ir(SPBOZ)$_2$ at a yield of 86%.

EXAMPLE 25

Synthesis of compound (PzDCA)$_2$Ir(DTylzPy)Ir(PzDCA)$_2$

Synthesis of (PzDCA)$_2$Ir(Cl)$_2$Ir(PzDCA)$_2$: 5 mmol of pyrazine-2,5-dicarboxylic acid(PzDCA) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PzDCA)$_2$Ir(Cl)$_2$Ir(PzDCA)$_2$ at a yield of 91%.

Synthesis of (PzDCA)$_2$Ir(DTylzPy)Ir(PzDCA)$_2$: 5 mmol of (PzDCA)$_2$Ir(Cl)$_2$Ir(PzDCA)$_2$ and 25 mmol of 3,7-diptolyl-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PzDCA)$_2$Ir(DTylzPy)Ir(PzDCA)$_2$ at a yield of 88%.

EXAMPLE 26

Synthesis of compound (PBOZ)$_2$Ir(bFPlzPy)Ir(PBOZ)$_2$

Synthesis of 3,7-bis(4-(trifluoromethyl)phenyl)-3H-imidazo[4,5-b]pyridine(bFPlzPy): 0.70 mol of $N^{2,}$4-bis (4-(trifluoromethyl)phenyl)pyridine-2,3-diamine and 2.56 mol of 2-(ethoxymethylene)malononitrile were added in 10 ml of isopropanol, and refluxed for 6 hours. The solution was removed and was purified by using column chromatography to thereby produce a solid crystalline product at a yield of 79%.

Synthesis of (PBOZ)$_2$Ir(Cl)$_2$Ir(PBOZ)$_2$: 5 mmol of 2-phenylbenzo[d]oxazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBOZ)$_2$Ir(Cl)$_2$Ir(PBOZ)$_2$ at a yield of 92%.

Synthesis of (PBOZ)$_2$Ir(bFPlzPy)Ir(PBOZ)$_2$: 5 mmol of (PBOZ)$_2$Ir(Cl)$_2$IrPBOZ)$_2$ and 25 mmol of 3,7-bis (4-(trifluoromethyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBOZ)$_2$Ir(bFPlzPy)Ir(PBOZ)$_2$ at a yield of 88%.

EXAMPLE 27

Synthesis of compound (PBTZ)$_2$Ir(bFPlzPy)Ir(PBTZ)$_2$

Synthesis of (PBTZ)$_2$Ir(Cl)$_2$Ir(PBTZ)$_2$: 5 mmol of 2-phenylbenzo[d]thiazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBTZ)$_2$Ir(Cl)$_2$Ir(PBTZ)$_2$ at a yield of 89%.

Synthesis of (PBTZ)$_2$Ir(bFPlzPy)Ir(PBTZ)$_2$: 5 mmol of (PBTZ)$_2$Ir(Cl)$_2$Ir(PBTZ)$_2$ and 25 mmol of 3,7-bis(4-(trifluoromethyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBTZ)$_2$Ir(bFPlzPy)Ir(PBTZ)$_2$ at a yield of 86%.

EXAMPLE 28

Synthesis of compound (F$_2$ppy)$_2$Ir(bFPlzPy)Ir(F$_2$ppy)$_2$

Synthesis of (F$_2$ppy)$_2$Ir(Cl)$_2$Ir(F$_2$ppy)$_2$: 5 mmol of 2-(2,4-difluorophenyl)pyridine and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (F$_2$ppy)$_2$Ir(Cl)$_2$Ir(F$_2$ppy)$_2$ at a yield of 86%.

Synthesis of (F$_2$ppy)$_2$Ir(bFPlzPy)Ir(F$_2$ppy)$_2$: 5 mmol of (F$_2$ppy)$_2$Ir(Cl)$_2$Ir(F$_2$ppy)$_2$ and 25 mmol of 3,7-bis(4-(trifluoromethyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (F$_2$ppy)$_2$Ir(bFPlzPy)Ir(F$_2$ppy)$_2$ at a yield of 85%.

EXAMPLE 29

Synthesis of compound (SPBOZ)$_2$Ir(bFPlzPy)Ir(SPBOZ)$_2$ (SPBOZ)$_2$Ir(Cl)$_2$Ir(SPBOZ)$_2$ synthesis: 5 mmol of 4-(4-(trimethylsilyl)phenyl)benzo[d]oxazole(SPBOZ) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (SPBOZ)$_2$Ir(Cl)$_2$Ir(SPBOZ)$_2$ at a yield of 87%.

Synthesis of (SPBOZ)$_2$Ir(bFPlzPy)Ir(SPBOZ)$_2$: 5 mmol of (SPBOZ)$_2$Ir(Cl)$_2$Ir(SPBOZ)$_2$ and 25 mmol of 3,7-bis(4-(trifluoromethyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(bFPlzPy)Ir(SPBOZ)$_2$ at a yield of 84%.

EXAMPLE 30

Synthesis of compound (PzDCA)$_2$Ir(bFPlzPy)Ir(PzDCA)$_2$

Synthesis of (PzDCA)$_2$Ir(Cl)$_2$Ir(PzDCA)$_2$: 5 mmol of pyrazine-2,5-dicarboxylic acid(PzDCA) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PzDCA)$_2$Ir(Cl)$_2$Ir (PzDCA)$_2$ at a yield of 92%.

Synthesis of (PzDCA)$_2$Ir(bFPlzPy)Ir(PzDCA)$_2$: 5 mmol of (PzDCA)$_2$Ir(Cl)$_2$Ir(PzDCA)$_2$ and 25 mmol of 3,7-bis(4-(trifluoromethyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PzDCA)$_2$Ir(bFPlzPy)Ir(PzDCA)$_2$ at a yield of 89%.

EXAMPLE 31

Synthesis of compound (PBOZ)$_2$Ir(bSPlzPy)Ir (PBOZ)$_2$

Synthesis of 3,7-bis(4-(trimethylsilyl)phenyl)-3H-imidazo[4,5-b]pyridine(bSPlzPy): N$^2$ 4-bis(4-(trimethylsilyl)phenyl)pyridine-2,3-diamine and 2.56 mol of 2-(ethoxymethylene)malonnitrile were added in 10 ml of isopropanol, and refluxed for 6 hours. The solution was removed and was purified by using column chromatography to thereby produce a solid crystalline product at a yield of 70%.

Synthesis of (PBOZ)$_2$Ir(Cl)$_2$Ir(PBOZ)$_2$: 5 mmol of 2-phenylbenzo[d]oxazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBOZ)$_2$Ir(Cl)$_2$Ir(PBOZ)$_2$ at a yield of 87%.

Synthesis of (PBOZ)$_2$Ir(bSPlzPy)Ir(PBOZ)$_2$: 5 mmol of (PBOZ)$_2$Ir(Cl)$_2$IrPBOZ)$_2$ and 25 mmol of 3,7-bis(4-(trimethylsilyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBOZ)$_2$Ir(bSPlzPy)Ir(PBOZ)$_2$ at a yield of 84%.

EXAMPLE 32

Synthesis of compound (PBTZ)$_2$Ir(bSPlzPy)Ir (PBTZ)$_2$

Synthesis of (PBTZ)$_2$Ir(Cl)$_2$Ir(PBTZ)$_2$: 5 mmol of 2-phenylbenzo[d]thiazole and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PBTZ)$_2$Ir(Cl)$_2$Ir(PBTZ)$_2$ at a yield of 85%.

Synthesis of (PBTZ)$_2$Ir(bSPlzPy)Ir(PBTZ)$_2$: 5 mmol of (PBTZ)$_2$Ir(Cl)$_2$Ir(PBTZ)$_2$ and 25 mmol of 3,7-bis(4-(trimethylsilyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (PBTZ)$_2$Ir(bSPlzPy)Ir(PBTZ)$_2$ at a yield of 83%.

EXAMPLE 33

Synthesis of compound (F$_2$ppy)$_2$Ir(bSPlzPy)Ir (F$_2$ppy)$_2$

Synthesis of (F$_2$ppy)$_2$Ir(Cl)$_2$Ir(F$_2$ppy)$_2$: 5 mmol of 2-(2,4-difluorophenyl)pyridine and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (F$_2$ppy)$_2$Ir(Cl)$_2$Ir(F$_2$ppy)$_2$ at a yield of 85%.

Synthesis of (F$_2$ppy)$_2$Ir(bSPlzPy)Ir(F$_2$ppy)$_2$: 5 mmol of (F$_2$ppy)$_2$Ir(Cl)$_2$Ir(F$_2$ppy)$_2$ and 25 mmol of 3,7-bis(4-(trimethylsilyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (F$_2$ppy)$_2$Ir(bSPlzPy)Ir(F$_2$ppy)$_2$ at a yield of 81%.

EXAMPLE 34

Synthesis of compound (SPBOZ)$_2$Ir(bSPlzPy)Ir(SPBOZ)$_2$

Synthesis of (SPBOZ)$_2$Ir(Cl)$_2$Ir(SPBOZ)$_2$: 5 mmol of 4-(4-(trimethylsilyl)phenyl)benzo[d]oxazole(SPBOZ) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (SPBOZ)$_2$Ir(Cl)$_2$Ir(SPBOZ)$_2$ at a yield of 82%.

Synthesis of (SPBOZ)$_2$Ir(bSPlzPy)Ir(SPBOZ)$_2$: 5 mmol of (SPBOZ)$_2$Ir(Cl)$_2$Ir(SPBOZ)$_2$ and 25 mmol of 3,7-bis(4-(trimethylsilyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce (SPBOZ)$_2$Ir(bSPlzPy)Ir(SPBOZ)$_2$ at a yield of 80%.

EXAMPLE 35

Synthesis of compound (PzDCA)$_2$Ir(bSPlzPy)Ir (PzDCA)$_2$

Synthesis of (PzDCA)$_2$Ir(Cl)$_2$Ir(PzDCA)$_2$: 5 mmol of pyrazine-2,5-dicarboxylic acid(PzDCA) and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (PzDCA)$_2$Ir(Cl)$_2$Ir (PzDCA)$_2$ at a yield of 84%.

Synthesis of (PzDCA)$_2$Ir(bSPlzPy)Ir(PzDCA)$_2$: 5 mmol of (PzDCA)$_2$Ir(Cl)$_2$Ir(PzDCA)$_2$ and 25 mmol of 3,7-bis(4-

(trimethylsilyl)phenyl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PzDCA)_2Ir(bSPlzPy)Ir(PzDCA)_2$ at a yield of 82%.

EXAMPLE 36

Synthesis of compound $(PBOZ)_2Ir(dNplzPy)Ir(PBOZ)_2$

Synthesis of 3,7-di(naphthalene-2-yl)-3H-imidazo[4,5-b]pyridine(dNplzPy): 0.70 mol of $N^2$,4-di(naphthalene-2-yl)pyridine-2,3-diamine and 2.56 mol of 2-(ethoxymethylene)malonnitrile were added in 10 ml of isopropanol, and refluxed for 6 hours. The solution was removed and was purified by using column chromatography to thereby produce a solid crystalline product at a yield of 74%.

Synthesis of $(PBOZ)_2Ir(Cl)_2Ir(PBOZ)_2$: 5 mmol of 2-phenylbenzo[d]oxazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBOZ)_2Ir(Cl)_2Ir(PBOZ)_2$ at a yield of 90%.

Synthesis of $(PBOZ)_2Ir(dNplzPy)Ir(PBOZ)_2$: 5 mmol of $(PBOZ)_2Ir(Cl)_2IrPBOZ)_2$ and 25 mmol of 3,7-di(naphthalene-2-yl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBOZ)_2Ir(dNplzPy)Ir(PBOZ)_2$ at a yield of 86%.

EXAMPLE 37

Synthesis of compound $(PBTZ)_2Ir(dNplzPy)Ir(PBTZ)_2$

Synthesis of $(PBTZ)_2Ir(Cl)_2Ir(PBTZ)_2$: 5 mmol of 2-phenylbenzo[d]thiazole and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBTZ)_2Ir(Cl)_2Ir(PBTZ)_2$ at a yield of 87%.

Synthesis of $(PBTZ)_2Ir(dNplzPy)Ir(PBTZ)_2$: 5 mmol of $(PBTZ)_2Ir(Cl)_2Ir(PBTZ)_2$ and 25 mmol of 3,7-di(naphthalene-2-yl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PBTZ)_2Ir(dNplzPy)Ir(PBTZ)_2$ at a yield of 83%.

EXAMPLE 38

Synthesis of compound $(F_2ppy)_2Ir(dNlpzPy)Ir(F_2ppy)_2$

Synthesis of $(F_2ppy)_2Ir(Cl)_2Ir(F_2ppy)_2$: 5 mmol of 2-(2,4-difluorophenyl)pyridine and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(F_2ppy)_2Ir(Cl)_2Ir(F_2ppy)_2$ at a yield of 83%.

Synthesis of $(F_2ppy)_2Ir(dNplzPy)Ir(F_2ppy)_2$: 5 mmol of $(F_2ppy)_2Ir(Cl)_2Ir(F_2ppy)_2$ and 25 mmol of 3,7-di(naphthalene-2-yl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(F_2ppy)_2Ir(dNplzPy)Ir(F_2ppy)_2$ at a yield of 82%.

EXAMPLE 39

Synthesis of compound $(SPBOZ)_2Ir(dNlzPy)Ir(SPBOZ)_2$

Synthesis of $(SPBOZ)_2Ir(Cl)_2Ir(SPBOZ)_2$: 5 mmol of 4-(4-(trimethylsilyl)phenyl)benzo[d]oxazole(SPBOZ) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(SPBOZ)_2Ir(Cl)_2Ir(SPBOZ)_2$ at a yield of 82%.

Synthesis of $(SPBOZ)_2Ir(dNplzPy)Ir(SPBOZ)_2$: 5 mmol of $(SPBOZ)_2Ir(Cl)_2Ir(SPBOZ)_2$ and 25 mmol of 3,7-di(naphthalene-2-yl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(SPBOZ)_2Ir(dNplzPy)Ir(SPBOZ)_2$ at a yield of 80%.

EXAMPLE 40

Synthesis of compound $(PzDCA)_2Ir(dNplzPy)Ir(PzDCA)_2$

Synthesis of $(PzDCA)_2Ir(Cl)_2Ir(PzDCA)_2$: 5 mmol of pyrazine-2,5-dicarboxylic acid(PzDCA) and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PzDCA)_2Ir(Cl)_2Ir(PzDCA)_2$ at a yield of 87%.

Synthesis of $(PzDCA)_2Ir(dNplzPy)Ir(PzDCA)_2$: 5 mmol of $(PzDCA)_2Ir(Cl)_2Ir(PzDCA)_2$ and 25 mmol of 3,7-di(naphthalene-2-yl)-3H-imidazo[4,5-b]pyridine, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtrated. The filtrate solution was purified by using column chromatography to thereby produce $(PzDCA)_2Ir(dNplzPy)Ir(PzDCA)_2$ at a yield of 83%.

TABLE 1

| compound | Yield (%) | PL (nm) |
|---|---|---|
| Compound 1 | 89 | 569 |
| Compound 2 | 87 | 571 |
| Compound 3 | 86 | 565 |
| Compound 4 | 84 | 574 |
| Compound 5 | 88 | 576 |
| Compound 6 | 83 | 571 |
| Compound 7 | 80 | 573 |
| Compound 8 | 79 | 568 |
| Compound 9 | 78 | 573 |
| Compound 10 | 81 | 574 |
| Compound 11 | 80 | 574 |
| Compound 12 | 76 | 577 |
| Compound 13 | 74 | 570 |
| Compound 14 | 70 | 579 |
| Compound 15 | 75 | 580 |
| Compound 16 | 81 | 561 |
| Compound 17 | 80 | 562 |
| Compound 18 | 78 | 557 |
| Compound 19 | 75 | 563 |
| Compound 20 | 79 | 566 |
| Compound 21 | 91 | 566 |
| Compound 22 | 90 | 567 |
| Compound 23 | 88 | 562 |
| Compound 24 | 86 | 568 |
| Compound 25 | 88 | 570 |
| Compound 26 | 88 | 562 |
| Compound 27 | 86 | 560 |
| Compound 28 | 85 | 557 |
| Compound 29 | 84 | 565 |
| Compound 30 | 89 | 567 |
| Compound 31 | 84 | 578 |
| Compound 32 | 83 | 576 |
| Compound 33 | 81 | 572 |
| Compound 34 | 80 | 580 |
| Compound 35 | 82 | 581 |
| Compound 36 | 86 | 564 |
| Compound 37 | 83 | 563 |
| Compound 38 | 82 | 560 |
| Compound 39 | 80 | 569 |
| Compound 40 | 83 | 570 |

EXAMPLE 41

As for an anode, a 10 Ω/cm² ITO substrate produced by the Corning Company was used. A hole injection layer was formed in a thickness of 60 nm by depositing IDE406 on top of the substrate in a vacuum condition. Subsequently, a hole transport layer was formed by depositing TPD chemical compound on top of the hole injection layer in a thickness of 30 nm in a vacuum condition. A light emitting layer was formed in a thickness of 20 nm by depositing a transition metal compound on top of the hole transport layer in a vacuum condition.

Subsequently, an HBL layer was formed in a thickness of 5 nm by depositing BCP on top of the light emitting layer in a vacuum condition. An electron transport layer (ETL) was formed in a thickness of 20 nm by depositing Alq3 on top of the light emitting layer in a vacuum condition. An organic electroluminescence device was completed by sequentially depositing LiF 1 nm and Al 300 nm on top of the electron transport layer in a vacuum condition to thereby form a LiF/Al electrode.

Simple modifications and alternations of the present invention can be easily made by the ordinary skilled person in the art within the spirit and scope of the appended claims.

The invention claimed is:

1. A metallic compound represented by the following Chemical Formula 1:

[Chemical Formula 1]

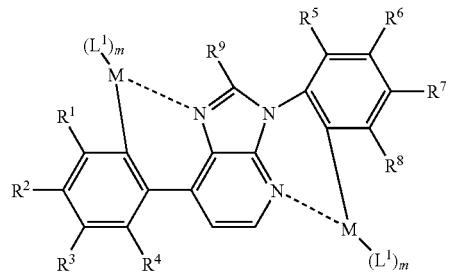

wherein M is a transition metal selected from Ir, Pt, Rh, Re and Os, m is 2, provided that the m is 1 when M is Pt, $R^1, R^2, R^3, R^4, R^5, R^6, R^7$, and $R^8$ are the same or different, and are selected from substituents of hydrogen, a C1 to C20 alkyl, an aryl, a cycloalkyl, a halogen, a linear or branched substituent including at least one halogen, a linear or branched substituent including at least one heteroatom, carbonyl, vinyl, and acetylenyl, or have a cyclic structure formed from substituents, $R^9$ is hydrogen, a C1 to C20 alkyl excluding an aromatic cyclic substituent, a cycloalkyl, a halogen, a linear or branched substituent including at least one halogen;

or a linear or branched substituent including at least one heteroatom, and $L^1$ is represented by the following Chemical Formula 2:

[Chemical Formula 2]

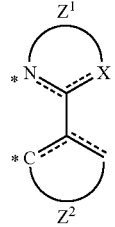

wherein $L^1$ in the above formula 2, is a independent ligand having a covalent bond site with a carbon denoted as * and a coordination bond with nitrogen and forming a complex compound with the transition metal M, and X is a hetero atom selected from nitrogen, oxygen, sulfur and phosporus, and $Z^1$ and $Z^2$ are atoms for forming a C4 to C7 aromatic hydrocarbon ring or aromatic heterocyclic ring and are represented by the following Chemical Formulae 4:

[Chemical Formulae 4]

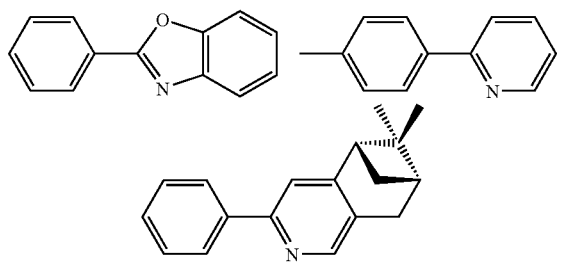

-continued
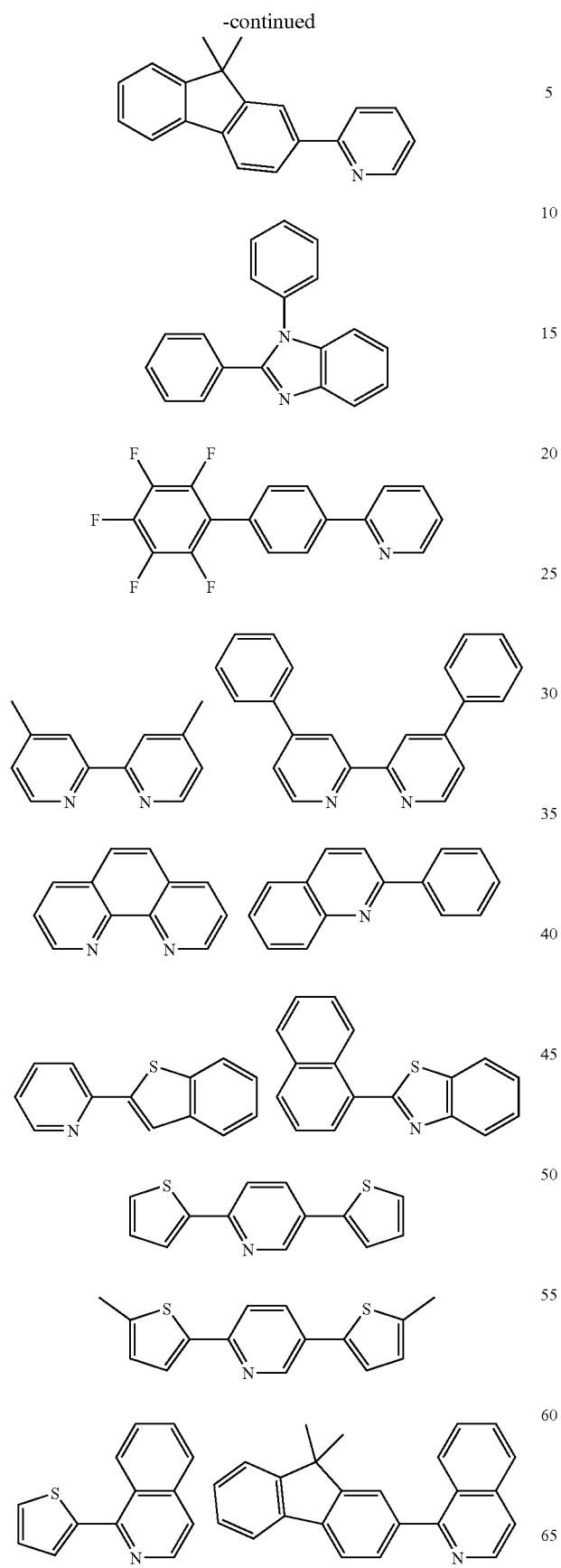
-continued
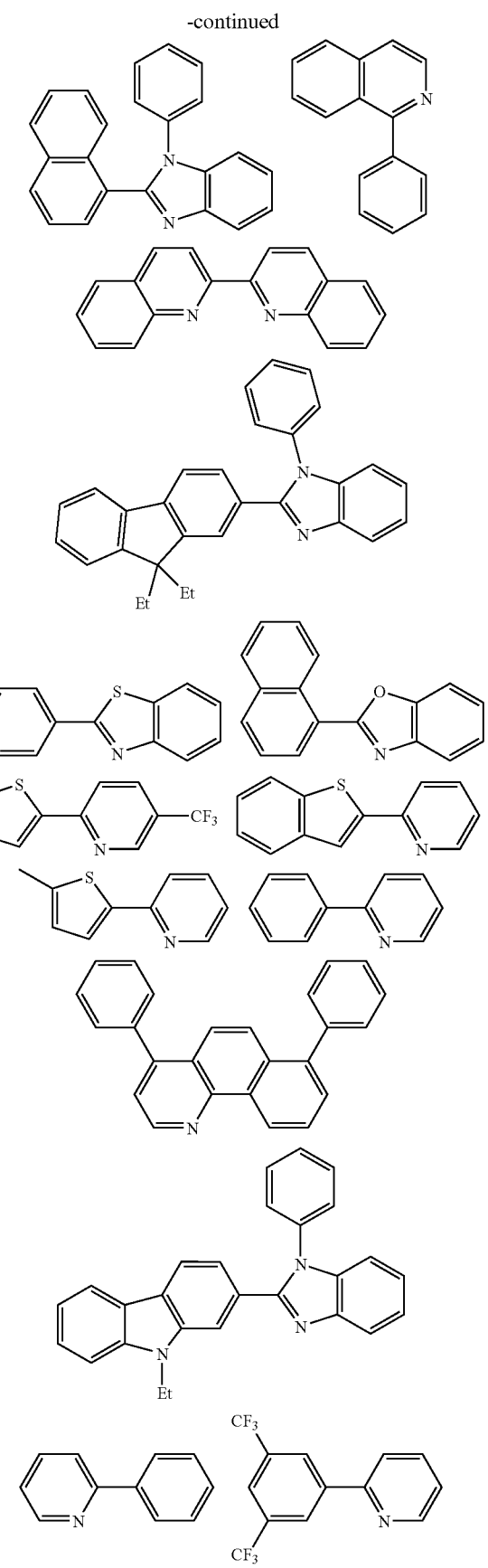

-continued
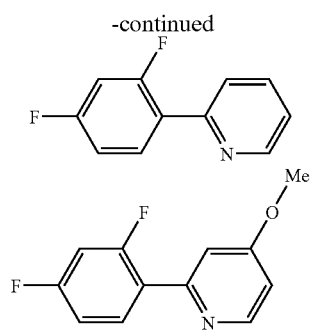
-continued
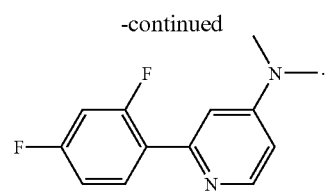
2. An organic electroluminescence device comprising the metallic compound of claim 1.
* * * * *

UNITED STATES PATENT AND TRADEMARK OFFICE
CERTIFICATE OF CORRECTION

PATENT NO. : 7,745,020 B2  Page 1 of 1
APPLICATION NO. : 11/910161
DATED : June 29, 2010
INVENTOR(S) : Dong-Hack Suh et al.

It is certified that error appears in the above-identified patent and that said Letters Patent is hereby corrected as shown below:

| Error Location in Issued Patent | | Description of Error and Correction |
|---|---|---|
| Column | Line | |
| Title Page | Item (86) | The correct date for PCT/KR2007/000114 should read January 8, 2007. Please change date from September 28, 2007 to January 8, 2007. |

Signed and Sealed this

Second Day of November, 2010

David J. Kappos
*Director of the United States Patent and Trademark Office*